United States Patent
Vinci et al.

(10) Patent No.: US 7,993,297 B2
(45) Date of Patent: Aug. 9, 2011

(54) APPARATUS FOR CONTROLLING BLOOD FLOW IN AN EXTRACORPOREAL BLOOD CIRCUIT

(75) Inventors: Luca Vinci, Poggio Rusco (IT); Francesco Fontanazzi, Modena (IT)

(73) Assignee: Gambro Lundia AB (SE)

( * ) Notice: Subject to any disclaimer, the term of this patent is extended or adjusted under 35 U.S.C. 154(b) by 0 days.

(21) Appl. No.: 12/471,818

(22) Filed: May 26, 2009

(65) Prior Publication Data
US 2010/0324465 A1 Dec. 23, 2010

Related U.S. Application Data

(63) Continuation of application No. 12/017,402, filed on Jan. 22, 2008, now Pat. No. 7,648,477, which is a continuation of application No. 10/500,331, filed as application No. PCT/IB02/05595 on Dec. 20, 2002, now Pat. No. 7,824,354.

(30) Foreign Application Priority Data

Dec. 27, 2001 (IT) .................................. TO01A1222

(51) Int. Cl.
*A61M 37/00* (2006.01)
*A61M 31/00* (2006.01)
*A61M 1/00* (2006.01)
*C02F 1/00* (2006.01)

(52) U.S. Cl. ...................... 604/4.01; 604/5.01; 604/6.09; 604/65; 604/67; 422/44; 210/742; 210/741

(58) Field of Classification Search ................. 604/4.01, 604/5.01, 609, 65, 67, 6.13, 28; 422/44, 422/46, 48; 210/742, 741, 143, 86, 87; 417/2–6, 417/18–22, 42, 43, 44.1
See application file for complete search history.

(56) References Cited

U.S. PATENT DOCUMENTS
3,882,861 A  5/1975 Kettering et al.
(Continued)

FOREIGN PATENT DOCUMENTS
DE  3720667  5/1989
(Continued)

OTHER PUBLICATIONS
PCT International Search Report issued for International Patent Application No. PCT/IB02/05595, dated May 9, 2003.
(Continued)

*Primary Examiner* — Jacqueline F. Stephens
(74) *Attorney, Agent, or Firm* — Finnegan, Henderson, Farabow, Garrett & Dunner, LLP

(57) ABSTRACT

Equipment for controlling blood flow in an extra-corporeal blood circuit, comprising at least a first sensor (11), designed to measure an arterial pressure (Part) upstream of a peristaltic pump (9); at least a second sensor (12), designed to measure an angular velocity (Ω) of the peristaltic pump; a memory (14) designed to store at least one set value (Qset) of the desired blood flow through the access branch, and a calibration function (F) in to at least the variables (v1), related to the angular velocity (Ω) of the pump, (v2), related to the arterial pressure (Part) in the portion of the said access branch upstream of the peristaltic pump, (v3), related to an actual flow of blood (Qactual) through the said access branch; and at least one control unit (13), capable of calculating an actual flow value (Qactual) by applying the function F to the values of angular velocity and arterial pressure (Part, Ω) measured by the sensors; comparing the actual flow (Qactual) with the desired flow (Qset); and varying the angular velocity of the said peristaltic pump if the Qactual–Qset lies outside a predetermined range.

48 Claims, 2 Drawing Sheets

U.S. PATENT DOCUMENTS

| | | | |
|---|---|---|---|
| 4,797,655 | A | 1/1989 | Orndal et al. |
| 4,995,268 | A | 2/1991 | Ash et al. |
| 5,057,278 | A | 10/1991 | Maxwell et al. |
| 5,092,836 | A | 3/1992 | Polaschegg |
| 5,261,874 | A | 11/1993 | Castle |
| 5,372,709 | A | 12/1994 | Hood |
| 5,588,959 | A | 12/1996 | Ahmad et al. |
| 5,733,257 | A | 3/1998 | Sternby |
| 5,866,015 | A | 2/1999 | Kramer |
| 5,947,692 | A | 9/1999 | Sahlin et al. |
| 6,284,131 | B1 | 9/2001 | Hogard et al. |
| 6,691,047 | B1 | 2/2004 | Fredericks |

FOREIGN PATENT DOCUMENTS

| | | |
|---|---|---|
| DE | 4013402 | 7/1991 |
| DE | 4003452 | 8/1991 |
| DE | 40 24 434 A1 | 2/1992 |
| DE | 19900320 | 6/2000 |
| DE | 101 12 848 A1 | 9/2001 |
| EP | 0 104 896 A2 | 4/1984 |
| EP | 0 315 312 A1 | 5/1989 |
| EP | 0 723 463 B1 | 7/1996 |
| EP | 0 773 035 B1 | 5/1997 |
| EP | 0 928 614 A1 | 7/1999 |
| EP | 1 044 695 A2 | 10/2000 |
| FR | 2244546 | 4/1975 |
| FR | 2 379 290 | 9/1978 |
| GB | 2 225 954 | 6/1990 |
| GB | 2 367 594 | 4/2002 |
| JP | 8-117483 | 5/1996 |
| JP | 8-182366 | 7/1996 |
| JP | 11-200928 | 7/1999 |
| JP | 11-328828 | 11/1999 |
| JP | 2001-504918 | 4/2001 |
| JP | 2001-276214 | 10/2001 |
| JP | 2001-298980 | 10/2001 |
| JP | 2001-321436 | 11/2001 |
| WO | WO 90/06781 | 6/1990 |
| WO | WO 91/09229 | 6/1991 |
| WO | WO 95/10310 | 4/1995 |
| WO | WO 97/10013 A1 | 3/1997 |

OTHER PUBLICATIONS

Decision of Rejection from the Japanese Patent Office relating to Japanese Patent Application No. 2003-556117, dated Aug. 19, 2009.

APPARATUS FOR CONTROLLING BLOOD FLOW IN AN EXTRACORPOREAL BLOOD CIRCUIT

This is a continuation of application Ser. No. 12/017,402, filed Jan. 22, 2008 now U.S. Pat. No. 7,648,477, which is a continuation of application Ser. No. 10/500,331, filed Jun. 28, 2004 now U.S. Pat. No. 7,824,354, and claims the benefit of International Application No. PCT/IB02/05595, filed on Dec. 20, 2002, and of Italian Application No. TO2001A001222 under 35 U.S.C. §119, all of which are incorporated herein by reference.

The present invention relates to equipment for controlling blood flow in an extracorporeal blood circuit.

In particular, the equipment to which the invention relates is designed to operate on extracorporeal circuits of blood treatment machines, for example machines for haemodialysis, haemofiltration, haemodiafiltration or plasmapheresis.

The machines for the treatments described above are typically used for processes of treating the blood of patients whose renal function is partially or totally compromised.

In particular, the blood treatment equipment indicated above typically comprises an extracorporeal circuit provided with at least one blood treatment unit, and with at least one access channel or branch designed to connect an area where blood is collected from the patient to a first chamber of the treatment unit; the extracorporeal circuit also comprises a second channel or return branch, extending downstream of the treatment unit from the said first chamber towards an area where the blood is returned to the patient.

In the access channel, there is also typically provided a peristaltic pump designed to act on the access channel to progressively move the blood flow towards the treatment unit.

It should be noted that, regardless of the type of dialysis treatment to be carried out on the patient, it is extremely important to know the precise quantity of blood collected from the patient and subsequently treated by the machine with which the extracorporeal blood circuit is associated.

In this respect, it should however be noted that the blood flow which can be obtained by using peristaltic pumps in the return portion of the extracorporeal circuit is actually dependent on various factors, the main ones of which are:
- the material, and consequently the elasticity, of the portion of line with which the peristaltic pump is associated;
- the geometry of the particular portion of the blood line with which the peristaltic pump is associated;
- the geometry of the pump rotor, and the angular velocity of the peristaltic pump;
- the pressure present, in particular, in the portions of tubing upstream and downstream of the peristaltic pump;
- the temperature of the extracorporeal circuit;
- the haematocrit value associated with the patient's blood;
- the geometry of the portion of tubing upstream of the pump;
- the geometry, and in particular the passage section, of the access member used to collect blood from the patient.

Formerly, when it was necessary to calculate the flow supplied by a peristaltic pump, this flow was considered to be proportional, according to a suitable conversion factor, to the instantaneous angular velocity of the pump.

In other words, the angular velocity of the pump segment was multiplied by a constant calibration factor in order to obtain a theoretical value of flow through the pump segment. According to circumstances, the resulting theoretical flow value was or was not shown on a suitable display of the machine.

However, because of the numerous factors mentioned briefly above, which affect the level of the flow actually supplied by the peristaltic pump, the calculation of the flow by means of a simple factor of proportionality with the angular velocity is clearly affected by errors which cannot be disregarded.

As will be easily understood, if, due to one or more of the described factors, the arterial pressure of the flow upstream of the pump reaches levels such that it impedes the movement of the blood flow provided by the peristaltic pump, the pump will produce an actual flow which is smaller than the estimated theoretical value. Moreover, an increase in the angular velocity set for the pump is accompanied by an increase in the pressure drop created upstream of the pump, which will evidently amplify the effects briefly described above.

Additionally, it must be emphasized that the pressure conditions upstream of the pump not only depend on the velocity and characteristics of the pump, but are also closely related to the form of access device (needle or other) used for connection to the patient's vascular system. In particular, in the case of needles, the procedures by which these needles are inserted into the patient's fistula, the conditions of the fistula, and the physiological condition and haematocrit value of the patient are all significant factors.

The actual flow produced by the pump can even vary during a single treatment as a result of variations in the arterial pressure upstream of the pump, which, evidently, significantly modify the mode of operation of the pump.

As mentioned above, the structure, in terms of materials and geometry, of the portion of tubing on which the pump acts can have a major effect on the flow which is actually generated by the peristaltic pump, where other conditions are held constant. In this connection, it should be noted that the dynamic behavior of the tubing portion and pump is variable, with respect to the time elapsing from the start of the treatment cycle, as a result of a deterioration, or more generally a variation, of the mechanical properties of the materials forming the line.

With the aim of overcoming the drawbacks described above, and of providing equipment for blood treatment in which it would be possible to know a flow value as close as possible to the flow actually passing through the pump portion of the extracorporeal circuit, U.S. Pat. No. 5,733,257 describes a method of calibrating a peristaltic pump, to be used with equipment provided with at least one internal flowmeter.

According to the invention described in the aforementioned patent, the method comprises the introduction of a fluid into the segment of tubing on which the pump acts, and the operation of the peristaltic pump at a constant rotation speed.

When the standard operating conditions have been reached, the pressure upstream of the portion of tubing on which the pump acts is measured, and the flow of fluid which actually passes through the pump portion is measured by means of the machine's internal flowmeter, in such a way that a pair of calibration values (actual flow and arterial pressure) are obtained as a function of the angular velocity of the pump which has been selected.

The process described above is repeated while the arterial pressure upstream of the pump is varied by suitable means in such a way as to obtain different pairs of values of arterial pressure and actual flow for a single value of angular velocity. At this point, a calibration curve is calculated, and used to determine a relationship between pressure and actual flow with respect to the angular velocity in question. By repeating the calibration criterion described above for different values of angular velocity, it is possible to create a set of calibration curves; when the machine is put into operation, the calibration curves are used to calculate the actual flow of the peristaltic pump, once the angular velocity of the pump and the pressure in the portion of tubing upstream of the pump have been determined by measurement. Also according to U.S. Pat. No. 5,733,257, it is possible to use the information on the actual flow obtained by means of the aforesaid calibration curves to control the angular velocity of the pump, in order to match the actual flow with that which is desired for the purposes of the particular treatment to be carried out on the patient.

Given these aspects of the prior art, one object of the present invention is to provide novel equipment controlling blood flow in an extracorporeal blood circuit, which is easily applied and which, in particular, makes it possible to control and know the actual flow passing through the peristaltic pump portion of the extracorporeal circuit, without any need to carry out preliminary calibration procedures on the machine, provided that the geometrical characteristics and the mechanical properties of the extracorporeal circuit are known.

In particular, a fundamental object of the invention is to provide novel equipment which enables the actual flow through the peristaltic pump portion to be determined and the peristaltic pump to be controlled by a feedback system, in order to make the actual flow which is generated essentially match the value which is set by the user or required by the treatment in progress.

A further and preferred object of the invention is to provide novel equipment which can also measure the actual flow with a close approximation, making allowance for the structural alteration undergone in time by the material of the portion of tubing on which the peristaltic pump acts.

These and further objects which will be made clearer by the following description are essentially achieved by equipment for controlling blood flow in an extracorporeal blood circuit according to what is described in the attached claim 1.

Further characteristics and advantages will be made clearer by the following description of some preferred, but not exclusive, embodiments of equipment for controlling blood flow in an extracorporeal blood circuit according to the invention.

This description is provided below with the aid of the attached drawings, provided solely for guidance and therefore without restrictive intent, in which.

Figure 1:
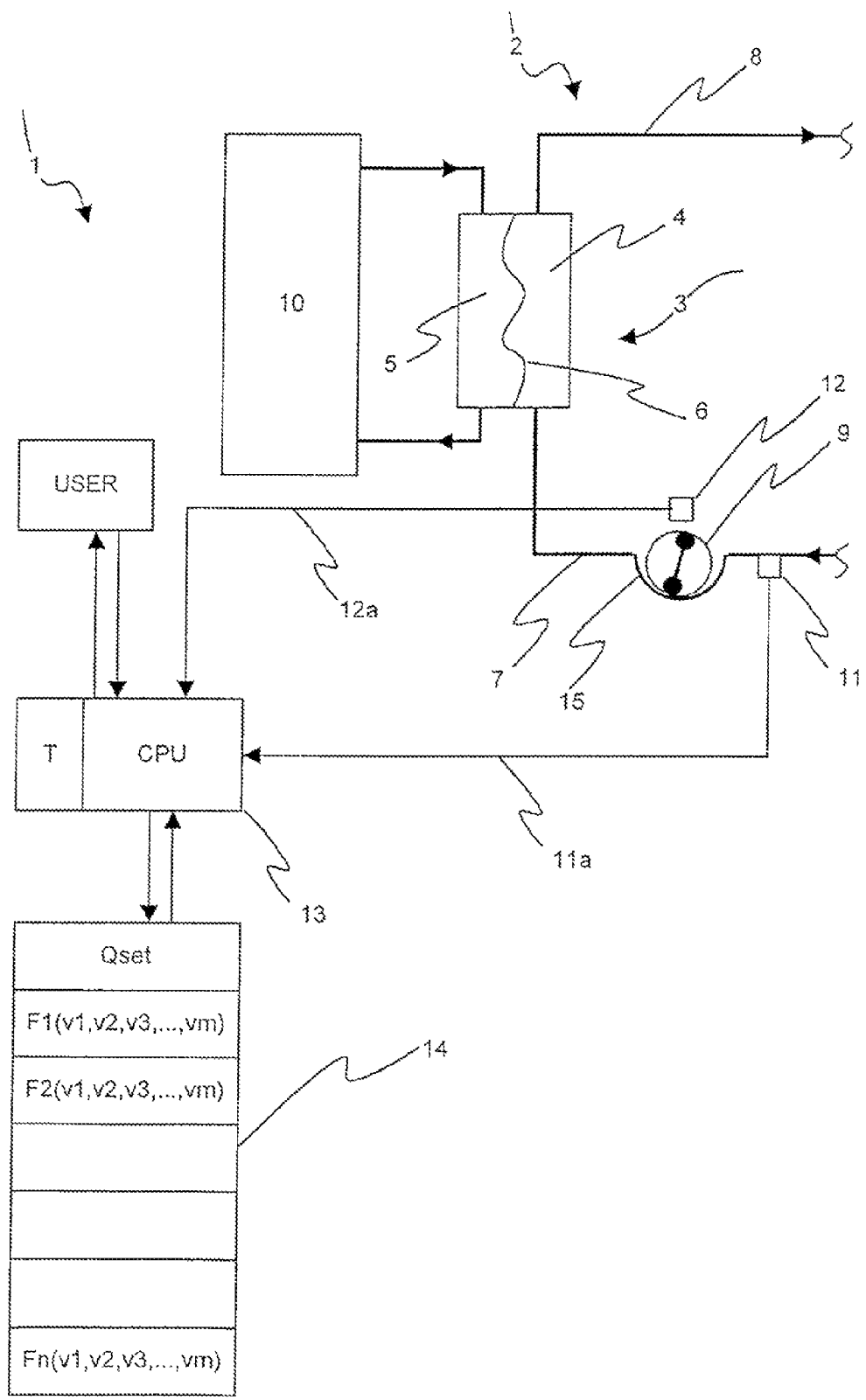
FIG. 1 is a schematic representation of equipment for controlling blood flow in an extracorporeal blood circuit according to the present invention.

With reference to the attached FIG. 1, this represents the whole of a piece of equipment for controlling blood flow in an extracorporeal blood circuit, which in turn is indicated by the number 2. The extracorporeal circuit 2 can be used, for example, for carrying out the extracorporeal circulation of blood, when the patient is to be subjected to treatments such as haemodialysis, haemofiltration, ultrafiltration, haemodiafiltration, or any other combination of the treatments listed here.

The extracorporeal circuit 2 conventionally comprises at least one blood treatment unit 3, formed by a first chamber 4 and at least one second chamber 5, separated from each other by a semi-permeable membrane 6. At least one access branch 7 extends between an area where blood is collected from a patient and the first chamber of the said treatment unit 4; at least one peristaltic pump 9 is associated for operation with a pump tube section 15 of the said access branch of the extracorporeal circuit, and at least one return branch 8 extends downstream of the treatment unit, between the aforesaid first chamber 4 and an area where the blood is returned to the patient. Typically, means (not illustrated) of access to the patient's cardiovascular system are provided in the areas where the blood is collected from the patient and returned to him, these means consisting, for example, of needles of appropriate dimensions, catheters, or access devices of other kinds. It should be noted that the second chamber of the unit 3 can be connected, for example, to a device 10 (not shown in detail) for sending a dialysis liquid towards the second chamber and for removing from the second chamber a dialysate in which the waste products and excess water from the blood have been accumulated.

The equipment for controlling the blood flow 1 has at least a first sensor 11, located in the access branch, in a portion of the said branch upstream of the peristaltic pump 9, in such a way that an arterial pressure (Part) can be measured and a corresponding output signal 11a proportional to the said arterial pressure can be generated. In practice, the first pressure sensor 11 operates immediately upstream of the peristaltic pump and can measure the pressure in the portion of tubing interposed between the area where the blood is collected from the patient and the said peristaltic pump. It should be noted that a negative pressure, typically with respect to atmospheric pressure, is typically found in this portion.

The equipment 1 also comprises a second sensor 12, associated for operation with the peristaltic pump and designed to measure an angular velocity $\omega$ (omega) of the said pump and to generate a corresponding second output signal 12a, proportional to the rotation speed of the peristaltic pump. It should be noted that the sensors described above are connected for operation to a control unit 13 to which the sensors send the first and the second signals respectively.

The control unit 13, consisting for example of a CPU, is associated with a memory 14, designed to store at least one set value (Qset) of the desired blood flow through the access branch, and a calibration function in the variables v1, v2, v3, which are described more fully below. In greater detail, v1 is a variable related to the angular velocity of the pump, v2 is a variable related to the arterial pressure (Part) present in the portion of the said access branch upstream of the said peristaltic pump, and v3 is a variable related to an actual blood flow (Qactual) through the said access branch.

The control unit 13 according to the invention can execute a control procedure comprising the following operations:
calculation of an actual flow value (Qactual) by application of the memory-resident calibration function F to the values of angular velocity ($\omega$) and arterial pressure (Part) measured by means of the first and second sensors, described briefly above;
comparison of the actual flow value (Qactual), calculated by means of the calibration function F, with the user-specified or memory-resident set flow value (Qset); it should be noted that the value Qset can be fixed or variable in time according to a profile determined by the treatment, depending on the requirements of the patient and the settings entered into the equipment;
variation of the angular velocity of the peristaltic pump when the difference between the actual flow and the desired flow (Qactual−Qset) is outside a predetermined acceptability range.

In practice, the control unit, by measuring the values of arterial pressure and angular velocity of the pump by means of the sensors, can use the calibration function to calculate the actual flow value and to correct the velocity of the pump when the actual flow differs excessively from the desired flow value through the access branch of the extracorporeal circuit.

The control unit, which is provided with a timer device, can execute the operations described above at predetermined time intervals.

Figure 2:
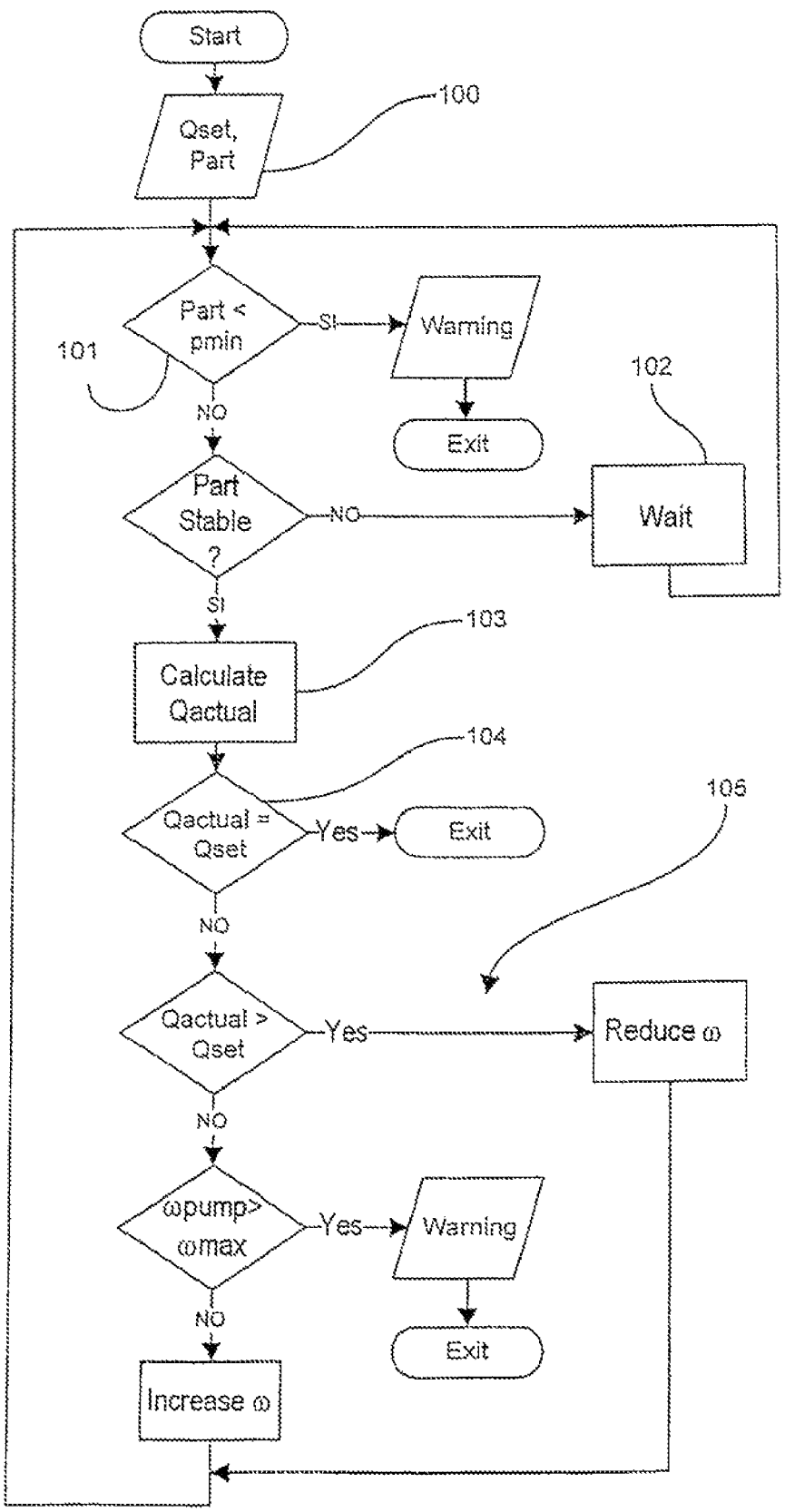
FIG. 2 is a flow diagram which illustrates schematically the steps of the procedure which can be executed, during the operation of the equipment, by a control unit associated with equipment for controlling blood flow in an extracorporeal blood circuit according to the present invention.

FIG. 2 is a flow diagram showing a possible operating mode of the control unit 13, according to the present invention. In terms of operation, the control unit can operate both in a first operating mode, in which it waits for signals for activating and disabling the previously described control procedure entered by means of a manual command of the user, through a user interface device 15, and by means of manual entry of the set flow (Qset). In other words, in the first manual operating mode, the control procedure is activated and disabled by a manual command of the operator in charge, who also manually enters the value of Qset.

Alternatively, the control unit can operate in a second operating mode, in which the previously described control procedure is activated at the start of the treatment, in a fully automatic way. Where the implementation is concerned, the control unit can be dedicated to the equipment for controlling blood flow described herein, or can alternatively be integrated into the central control system of the machinery with which the equipment in question is associated.

Moving on to a more detailed analysis of the operating steps executed by the control unit of the equipment in question (see FIG. 2 for reference), we can see that the control unit must initially receive an activation signal, in the form of a manual command or a suitable automatic activation signal (Start in FIG. 2) received following the execution of a particular treatment by the machinery with which the control equipment is associated. It should be noted that the control unit can activate the control procedure not only after an activation signal has been received, but also if, for any reason, the value of Qset or of the arterial pressure Part varies or is varied (block 100 in FIG. 2).

When the control procedure has been activated, the control unit reads the set value of Qset and the actual value of Part; the control unit then executes a step of verifying the stability of the arterial pressure Part (block 101), by commanding the measurement of the said arterial pressure at a predetermined instant T1 and at a successive instant T2, and by making a comparison between the difference between the arterial pressures at the instants T1 and T2 and a predetermined range of acceptability; if the arterial pressure is not stable, or in other words if $\Delta P = Part (T1) - Part (T2)$ falls outside a range of acceptability, the control unit waits for a predetermined time interval (block 102) and then repeats the steps of measuring the arterial pressure at two successive time intervals to verify its stabilization. When the stability of the arterial pressure has been verified, the control unit 13 commands the continuation of the procedure which comprises the calculation of the value of the actual flow Qactual (block 103), the subsequent comparison of the actual flow Qactual with the set flow value Qset (block 104) and the subsequent variation of the angular velocity of the peristaltic pump, if Qactual−Qset does not lie within a range of acceptability (blocks 105).

As shown in FIG. 2, a step of comparing the value of Part with a threshold value considered critical for the treated patient is specified before the variation of the angular velocity of the peristaltic pump. If the pressure is below this threshold value, the algorithm is exited and the operator is alerted, by a warning message relating to the occurrence of a limit pressure condition. Similarly, and particularly if the angular velocity of the pump has to be increased, a step of comparing the angular velocity of the peristaltic pump before the variation with an acceptable maximum velocity of the said peristaltic pump is executed. If the peristaltic pump has already reached a maximum value of angular velocity which it is undesirable to exceed, the control unit stops the procedure and sends a warning signal to the user interface, to inform the user that a limit velocity condition has been reached by the peristaltic pump, this condition evidently preventing the system from controlling the pump appropriately in order to provide an actual flow Qactual essentially equal to the desired value (Qset) which has been set.

It should be noted that the calibration function F can also have at least one further variable v4 related to a time (Ti) elapsed from the start of the administered treatment. In practice, as soon as the treatment starts, the control unit stores a time data element relating to the instant of starting; the control unit can determine the time elapsed between the said instant of starting and each instant at which the said control procedure is executed, and can then calculate an actual flow value (Qactual) by applying the memory-resident calibration function F to the value of the said elapsed time (Ti) and to the values of angular velocity and arterial pressure (Part, ω) measured by means of the said sensors.

In a first embodiment of the invention, the calibration function F is of the type $v3 = [\Sigma_{i=0 \ldots n} a_i \cdot (v2)^{n-i} \cdot (v1)^i] + C$, where $a_i$ and C are experimentally determined known parameters. More simply, the calibration function F can be of the type $v3 = a \cdot v1 + b \cdot v1 \cdot v2 + c \cdot v2 + d$, where a, b, c, d are the experimentally determined known parameters, and where v1 is the angular velocity of the pump, v2 is the arterial pressure Part in the portion of the said access branch upstream of the said peristaltic pump, and v3 is an actual blood flow (Qactual) through the said access branch.

In particular, it was found that the following values of a, b, c, d (divided into two sets, each valid for a predetermined pressure range Part) can be used to obtain a suitable calibration function; in practice, the function F Comprises two functions, F' and F", linked together with continuity, the first F' being valid in a first range of values of arterial pressure, and the second F" being valid in a second range of values of arterial pressure which follows the said first range.

Alternatively, when F is also a function of v, the calibration function F is of the type $v3 = [\Sigma_{i=0 \ldots n} \Sigma_{k=0 \ldots m} a_i \cdot b_k \cdot (v2)^{n-i-k} \cdot (v1)^i \cdot (v4)^k] + C$, where $a_i$ $b_k$ and C are experimentally determined known parameters. In this second case, the function F can be, more specifically, of the type $v3 = (a \cdot v1 + b \cdot v1 \cdot v2 + c \cdot v2 + d) \cdot f(v4)$, where a, b, c, d are experimentally determined known parameters and f(v4) is a function which is also known and experimentally determined in the variable v4.

It should also be emphasized that the memory 14 can be designed to store a plurality of calibration functions F1, F2, . . . Fn, each at least in the variables v1, v2, v3 and if appropriate in the variable v4. Each of these calibration functions can in practice be applicable to a corresponding type of extracorporeal circuit. More precisely, if multiple types of extracorporeal circuit are in production, with pump tube portions differing from each other, for example in respect of materials and/or geometry or other characteristics, a corresponding appropriate calibration function can be provided for and associated with each of these types, and can be stored in the memory 14. Each function F can also be associated with a corresponding identification code of the corresponding extracorporeal circuit, so that the user can simply select the type of circuit installed and thus automatically select the corresponding function F to be used for the calculation of Qactual. Finally, it should be specified that the function F can also be a function of one or more of the following additional variables: v5, related to the geometric characteristics of an access member connectable for operation to the said extracorporeal circuit; v6, related to the length of the portion of tube of the access branch upstream of the said peristaltic pump; v7, related to the pressure in the portion of access branch downstream of the peristaltic pump; v8, related to the temperature of the extracorporeal circuit; and v9, related to the haematocrit value of the blood of the treated patient.

In practice, when a plurality of previously stored functions F is available, each relating to a corresponding type of extracorporeal circuit, and each capable of allowing for the rotation speed of the pump, the pressure Part, the time elapsed from the start of the use of the circuit, the type of access member in use and the length of the line upstream of the pump, it is possible to provide a reliable determination of Qactual and a simple and flexible instrument for controlling the peristaltic pump.

The invention also relates to a software program comprising instructions for making a control unit, whether of the dedicated type or associated with the machinery of which the extracorporeal circuit is a subordinate component, capable of executing the steps of the control procedure described above. From the practical point of view, this program can be stored on a magnetic and/or optical recording medium, in a read only memory, or in a volatile computer memory, or can be carried by an electric or electromagnetic carrier. Finally, the invention also comprises a machine for blood treatment, which is capable of carrying out one or more of the following treatments:

haemodialysis,
haemofiltration,
haemodiafiltration,
pure ultrafiltration,
plasmapheresis, and which is also provided with equipment for controlling blood flow in an extracorporeal circuit as described and illustrated in the attached drawings.

The invention claimed is:

1. An apparatus for controlling blood flow in an extracorporeal blood circuit, said extracorporeal blood circuit having at least one blood treatment unit, at least one access branch extending between a blood collection area, where blood is collected from a patient, and the at least one blood treatment unit, at least one peristaltic pump associated for operation with said access branch of the extracorporeal blood circuit, and at least one return branch extending between the at least one blood treatment unit and a blood return area, where the blood is returned to the patient, said apparatus comprising:

at least a first sensor means for measuring an arterial pressure in a portion of said at least one access branch upstream of the at least one peristaltic pump and for generating a corresponding first output signal proportional to said arterial pressure;

at least a second sensor means for measuring an angular velocity of the at least one peristaltic pump and for generating a corresponding second output signal proportional to the angular velocity of said at least one peristaltic pump;

a memory means for storing at least one set flow value of a desired blood flow through said access branch, measured values of arterial pressure and angular velocity, and a calibration function in accordance with at least the following variables:

v1, related to the angular velocity of the pump;

v2, related to the arterial pressure in the portion of said at least one access branch upstream of the at least one peristaltic pump;

v3, related to an actual flow of blood through said at least one access branch; and v4, related to a time elapsed from a start condition of said control procedure; at least one control unit, operatively coupled to said first and second sensor means and to said memory means for receiving said first and second output signals and for storing corresponding measured values of arterial pressure and angular velocity in said memory means, said control unit including means for executing a control procedure, the means for executing the control procedure comprising:

means for calculating an actual flow value by applying said calibration function to the corresponding measured values of arterial pressure and angular velocity;

means for comparing said actual flow value with said at least one set flow value;

means for varying the angular velocity of said at least one peristaltic pump if the difference between the actual flow and the desired flow lies outside a predetermined range, wherein the means for executing a control procedure further comprises means for determining a time elapsed between said start condition and each instant in which said control procedure is executed, and said means for calculating the actual flow value applies said calibration function to a value of said time elapsed and to the corresponding measured values of arterial pressure and angular velocity.

2. An apparatus according to claim 1, the control unit is provided with a timer means for executing said control procedure at predetermined time intervals.

3. An apparatus according to claim 1, wherein said means for executing the control procedure further comprises means for verifying a stability of said arterial pressure.

4. An apparatus according to claim 3, wherein the means for verifying a stability of said arterial pressure further comprises:

means for measuring a first arterial pressure at a predetermined time, means for measuring a second arterial pressure after said predetermined time, means for comparing a difference between the first and second arterial pressures with a predetermined range of acceptability, means for waiting for a predetermined time interval, and means for repeating a measurement of a first arterial pressure and a second arterial pressure and for comparing a difference between the repeated measurement of the first and second arterial pressures.

5. An apparatus according to claim 3, wherein said means for executing the control procedure is for controlling said means for verifying a stability of the arterial pressure to verify said arterial pressure stability before said means for calculating an actual flow calculate the actual blood flow.

6. A blood treatment machine comprising the apparatus for controlling the blood flow according to claim 5.

7. An apparatus according to claim 1, wherein said means for executing the control procedure is for controlling said means for calculating an actual flow value to calculate said actual flow value before said means for comparing said actual flow value with said at least one set flow value compare said actual flow value with said at least one set flow value;

said means for executing the control procedure also being configured to control the means for comparing said actual flow value with said at least one set flow value to compare said actual flow value with said at least one set flow value before the means for varying the angular velocity of said at least one peristaltic pump vary the angular velocity of said at least one peristaltic pump.

8. An apparatus according to claim 7, wherein said means for executing the control procedure includes a means for comparing the arterial pressure with a threshold value considered critical for a patient being treated, and means for generating an operator warning message relating to an occurrence of a limit pressure condition if the arterial pressure is below the threshold value,
wherein said means for executing the control procedure is for controlling said means for generating an operator warning message to generate, if the arterial pressure is below the threshold value, an operator warning message after the means for comparing the actual flow value with said set flow value have compared the actual flow value with said set flow value and before said means for varying the angular velocity of said at least one peristaltic pump varies the angular velocity of said at least one peristaltic pump.

9. An apparatus according to claim 7, wherein said means for executing a control procedure further comprises means of comparing the angular velocity with an acceptable maximum angular velocity value which can be imparted to the pump,
wherein said means for executing a control procedure is for controlling said means for comparing the angular velocity with an acceptable maximum angular velocity value which can be imparted to the pump to compare the angular velocity with an acceptable maximum angular velocity value which can be imparted to the pump after said means for comparing said actual flow value with said set flow value have compared said actual flow value with said set flow value and before said means for varying the angular velocity of said peristaltic pump vary the angular velocity of said peristaltic pump.

10. An apparatus according to claim 1, wherein $v3 = [\Sigma_{i=0\ldots n} a_i \cdot (v2)^{n-i} \cdot (v1)^i] + C$, where $a_i$ and C are experimentally determined known parameters.

11. An apparatus according to claim 10, wherein $v3 = a \cdot v1 + b \cdot v1 \cdot v2 + c \cdot v2 + d$, where a, b, c, and d are experimentally determined known parameters.

12. A blood treatment machine comprising the apparatus for controlling the blood flow according to claim 10.

13. An apparatus according to claim 1, wherein $v3 = [\Sigma_{i=0\ldots n} \Sigma_{k=0\ldots m} a_i \cdot b_k \cdot (v2)^{n-i-k} \cdot (v1)^i \cdot (v4)^k] + C$, where $a_i$, $b_k$ and C are experimentally determined known parameters.

14. An apparatus according to claim 13, wherein $v3 = (a \cdot v1 + b \cdot v1 \cdot v2 + c \cdot v2 + d) \cdot f(v4)$, where a, b, c, and d are experimentally determined known parameters and $f(v4)$ is a function which is also known and experimentally determined in a variable v4.

15. An apparatus according to claim 1, wherein said memory means stores a plurality of calibration functions, each based upon at least variables v1, v2, and V3, and each applicable to a corresponding one of a plurality of types of extracorporeal circuits.

16. An apparatus according to claim 15, wherein each of said calibration functions comprises the further variable v4, related to a time elapsed from a start condition of said control procedure.

17. An apparatus according to claim 16, wherein each of said calibration functions comprises the further variables:
v5, related to geometrical characteristics of an access member connectable for operation to said extracorporeal blood circuit; and
v6, related to a length of a portion of a tube of the at least one access branch upstream of said at least one peristaltic pump.

18. A blood treatment machine comprising the apparatus for controlling the blood flow according to claim 17.

19. An apparatus according to claim 17, wherein said calibration function comprises two functions linked together with continuity, the first function being valid in a first range of values of arterial pressure, and the second function being valid in a second range of values of arterial pressure following said first range.

20. An apparatus according to claim 1, further comprising a user interface means for sending the control unit at least one signal activating said control procedure and at least one signal disabling said control procedure.

21. An apparatus according to claim 1, wherein the control unit comprises a programmed CPU.

22. An apparatus according to claim 21, wherein the means for executing a control procedure comprises a software program means programming said CPU, said software program means being stored in said memory means and being executed by the CPU.

23. A blood treatment machine comprising the apparatus for controlling the blood flow according to claim 22.

24. A blood treatment machine comprising the apparatus for controlling the blood flow according to claim 1.

25. An apparatus for controlling blood flow in an extracorporeal blood circuit, said extracorporeal blood circuit having at least one blood treatment unit, at least one access branch extending between a blood collection area, where blood is collected from a patient, and the at least one blood treatment unit, at least one peristaltic pump associated for operation with said access branch of the extracorporeal blood circuit, and at least one return branch extending between the at least one blood treatment unit and a blood return area, where the blood is returned to the patient, said apparatus comprising:
at least a first sensor means for measuring an arterial pressure in a portion of said at least one access branch upstream of the at least one peristaltic pump and for generating a corresponding first output signal proportional to said arterial pressure;
at least a second sensor means for measuring an angular velocity of the at least one peristaltic pump and for generating a corresponding second output signal proportional to the angular velocity of said at least one peristaltic pump;
a memory means for storing at least one set flow value of a desired blood flow through said access branch, measured values of arterial pressure and angular velocity, and a calibration function in accordance with at least the following variables:
v1, related to the angular velocity of the pump;
v2, related to the arterial pressure in the portion of said at least one access branch upstream of the at least one peristaltic pump; and
v3, related to an actual flow of blood through said at least one access branch;
at least one control unit, operatively coupled to said first and second sensor means and to said memory means for receiving said first and second output signals and for storing corresponding measured values of arterial pressure and angular velocity in said memory means, said control unit including means for executing a control procedure, the means for executing the control procedure comprising:
means for verifying a stability of said arterial pressure;
means for calculating an actual flow value by applying said calibration function to the corresponding measured values of arterial pressure and angular velocity;
means for comparing said actual flow value with said at least one set flow value;
means for varying the angular velocity of said at least one peristaltic pump if the difference between the actual flow and the desired flow lies outside a predetermined range.

26. An apparatus according to claim 25, the control unit is provided with a timer means for executing said control procedure at predetermined time intervals.

27. An apparatus according to claim 25, wherein the means for verifying a stability of said arterial pressure further comprises:
means for measuring a first arterial pressure at a predetermined time,
means for measuring a second arterial pressure after said predetermined time,
means for comparing a difference between the first and second arterial pressures with a predetermined range of acceptability,
means for waiting for a predetermined time interval, and means for repeating a measurement of a first arterial pressure and a second arterial pressure and for comparing a difference between the repeated measurement of the first and second arterial pressures.

28. An apparatus according to claim 25, wherein said means for executing the control procedure is for controlling said means for verifying a stability of the arterial pressure to verify said arterial pressure stability before said means for calculating an actual flow calculate the actual blood flow.

29. A blood treatment machine comprising the apparatus for controlling the blood flow according to claim 28.

30. An apparatus according to claim 25, wherein said means for executing the control procedure is for controlling said means for calculating an actual flow value to calculate said actual flow value before said means for comparing said actual flow value with said at least one set flow value compare said actual flow value with said at least one set flow value;
said means for executing the control procedure also being for controlling the means for comparing said actual flow value with said at least one set flow value to compare said actual flow value with said at least one set flow value before the means for varying the angular velocity of said at least one peristaltic pump vary the angular velocity of said at least one peristaltic pump.

31. An apparatus according to claim 30, wherein said means for executing the control procedure includes a means for comparing the arterial pressure with a threshold value considered critical for a patient being treated, and means for generating an operator warning message relating to an occurrence of a limit pressure condition if the arterial pressure is below the threshold value,
wherein said means for executing the control procedure is for controlling said means for generating an operator warning message to generate, if the arterial pressure is below the threshold value, an operator warning message after the means for comparing the actual flow value with said set flow value have compared the actual flow value with said set flow value and before said means for varying the angular velocity of said at least one peristaltic pump varies the angular velocity of said at least one peristaltic pump.

32. An apparatus according to claim 30, wherein said means for executing a control procedure further comprises means of comparing the angular velocity with an acceptable maximum angular velocity value which can be imparted to the pump,
wherein said means for executing a control procedure is for controlling said means for comparing the angular velocity with an acceptable maximum angular velocity value which can be imparted to the pump to compare the angular velocity with an acceptable maximum angular velocity value which can be imparted to the pump after said means for comparing said actual flow value with said set flow value have compared said actual flow value with said set flow value and before said means for varying the angular velocity of said peristaltic pump vary the angular velocity of said peristaltic pump.

33. An apparatus according to claim 25, wherein the calibration function comprises the following further variable:
V4, related to a time elapsed from a start condition of said control procedure, said control unit further comprising a means for determining a time elapsed between said start condition and each instant in which said control procedure is executed, and means for calculating an actual flow value by applying said calibration function to a value of said time elapsed and to the corresponding measured values of arterial pressure and angular velocity.

34. An apparatus according to claim 33, wherein $$v3=[\Sigma_{i=0\ldots n}\Sigma_{k=0\ldots m} a_i \cdot b_k \cdot (v2)^{n-i-k} \cdot (v1)^i \cdot (v4)^k]+C,$$

where $a_i$, $b_k$ and C are experimentally determined known parameters.

35. An apparatus according to claim 34, wherein $$v3=(a.v1+b.v1.v2+c.v2+d).f(v4),$$

where a, b, c, and d are experimentally determined known parameters and f(v4) is a function which is also known and experimentally determined in a variable v4.

36. A blood treatment machine comprising the apparatus for controlling the blood flow according to claim 33.

37. An apparatus according to claim 25, wherein $$v3=[\Sigma_{i=\ldots n} a_i \cdot (v2)^{n-i} \cdot (v1)^i]+C,$$

wherein $a_i$ and C are experimentally determined known parameters.

38. An apparatus according to claim 37, wherein $$v3=a.v1+b.v1.v2+c.v2+d,$$

where a, b, c, and d are experimentally determined known parameters.

39. An apparatus according to claim 25, wherein said memory means stores a plurality of calibration functions, each based upon at least variables v1, v2, and v3, and each applicable to a corresponding one of a plurality of types of extracorporeal circuits.

40. An apparatus according to claim 39, wherein each of said calibration functions comprises the further variable v4, related to a time elapsed from a start condition of said control procedure.

41. An apparatus according to claim 40, wherein each of said calibration functions comprises the further variables:
v5, related to geometrical characteristics of an access member connectable for operation to said extracorporeal blood circuit; and
v6, related to a length of a portion of a tube of the at least one access branch upstream of said at least one peristaltic pump.

42. A blood treatment machine comprising the apparatus for controlling the blood flow according to claim 41.

43. An apparatus according to claim 41, wherein said calibration function comprises two functions linked together with continuity, the first function being valid in a first range of values of arterial pressure, and the second function being valid in a second range of values of arterial pressure following said first range.

44. An apparatus according to claim 25, further comprising a user interface means for sending the control unit at least one signal activating said control procedure and at least one signal disabling said control procedure.

45. An apparatus according to claim 25, wherein the control unit comprises a programmed CPU.

46. An apparatus according to claim 45, wherein the means for executing a control procedure comprises a software program means programming said CPU, said software program means being stored in said memory means and being executed by the CPU.

47. A blood treatment machine comprising the apparatus for controlling the blood flow according to claim 46.

48. A blood treatment machine comprising the apparatus for controlling the blood flow according to claim 25.

\* \* \* \* \*

UNITED STATES PATENT AND TRADEMARK OFFICE
CERTIFICATE OF CORRECTION

PATENT NO. : 7,993,297 B2
APPLICATION NO. : 12/471818
DATED : August 9, 2011
INVENTOR(S) : Luca Vinci et al.

Page 1 of 1

It is certified that error appears in the above-identified patent and that said Letters Patent is hereby corrected as shown below:

In Claim 37, col. 12, line 43, "$v3 = [\Sigma_{i=...n}\ a_i \bullet (v2)^{n-i} \bullet (v1)^i] + C,$" should read --$v3 = [\Sigma_{i=0...n}\ a_i \bullet (v2)^{n-i} \bullet (v1)^i] + C,$--.

Signed and Sealed this
Eighth Day of November, 2011

David J. Kappos
*Director of the United States Patent and Trademark Office*